(12) United States Patent
Sumiyoshi

(10) Patent No.: US 9,429,549 B2
(45) Date of Patent: Aug. 30, 2016

(54) CHROMATOGRAPH MASS SPECTROMETER

(71) Applicant: SHIMADZU CORPORATION, Kyoto-shi, Kyoto (JP)

(72) Inventor: Takashi Sumiyoshi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/431,806

(22) PCT Filed: Sep. 28, 2012

(86) PCT No.: PCT/JP2012/075054
§ 371 (c)(1),
(2) Date: Mar. 30, 2015

(87) PCT Pub. No.: WO2014/049823
PCT Pub. Date: Apr. 3, 2014

(65) Prior Publication Data
US 2015/0247829 A1 Sep. 3, 2015

(51) Int. Cl.
*H01J 49/26* (2006.01)
*G01N 30/72* (2006.01)
*G01N 30/86* (2006.01)
*H01J 49/00* (2006.01)

(52) U.S. Cl.
CPC .......... *G01N 30/72* (2013.01); *G01N 30/8651* (2013.01); *H01J 49/0031* (2013.01)

(58) Field of Classification Search
USPC ...... 250/281, 282, 283, 288; 702/22, 23, 24, 702/25, 26, 27, 28, 29, 30
See application file for complete search history.

(56) References Cited

U.S. PATENT DOCUMENTS

| | | | | |
|---|---|---|---|---|
| 8,168,942 | B2 * | 5/2012 | Sumiyoshi | 250/281 |
| 8,735,809 | B2 * | 5/2014 | Sumiyoshi | 250/282 |
| 2008/0206737 | A1 * | 8/2008 | Hunter | G01N 33/68 435/4 |

FOREIGN PATENT DOCUMENTS

| | | |
|---|---|---|
| JP | 2003-172726 A | 6/2003 |
| JP | 2012-132799 A | 7/2012 |

OTHER PUBLICATIONS

International Search Report for PCT/JP2012/075054 dated Nov. 13, 2012 English Translation.

* cited by examiner

*Primary Examiner* — Nicole Ippolito
(74) *Attorney, Agent, or Firm* — Sughrue Mion, PLLC

(57) ABSTRACT

Segments into which time is divided are set at a point where predicted elution time ranges of compounds in a compound table do not overlap. One or more compounds are allotted to each segment. Subsequently, the dwell time per ion is calculated in each segment, based on the number of assigned compounds, loop time and the like. If the dwell time is shorter than the lower limit value (No in S6), the one segment is forcedly subdivided such that each subdivision include a predetermined number of compounds (S7). A compound having an elution time range trespassing the new segment boundary is allotted as a measurement target to both segments across the boundary (S8). If the dwell time is of at least the lower limit in every segment regenerated by the subdivision (Yes in S9), the process for this segment is finished. Such subdivision and compound reassignment in every segment can automatically create a parameter table for a measurement method capable of achieving high quantitativeness.

3 Claims, 15 Drawing Sheets

Fig. 8

| No | COMPOUND NAME | SEGMENT | MEASUREMENT START TIME (min) | MEASUREMENT END TIME (min) | EVENT TIME (msec) | MEASUREMENT TARGET ION m/z-1 | MEASUREMENT TARGET ION m/z-2 | DWELL TIME (msec) |
|---|---|---|---|---|---|---|---|---|
| 1 | A | 1 | 10.022 | 10.260 | 43 | 127 | 79 | 20.5 |
| 2 | B | 1 | 10.022 | 10.260 | 43 | 173 | 109 | 20.5 |
| 3 | C | 1 | 10.022 | 10.260 | 43 | 151 | 108 | 20.5 |
| 4 | D | 1 | 10.022 | 10.260 | 43 | 306 | 160 | 20.5 |
| 5 | E | 1 | 10.022 | 10.260 | 43 | 216 | 138 | 20.5 |
| 6 | F | 1 | 10.022 | 10.260 | 43 | 292 | 160 | 20.5 |
| 7 | G | 1 | 10.022 | 10.260 | 42 | 127 | 79 | 20 |
| 8 | A | 2 | 10.260 | 10.375 | 30 | 127 | 79 | 14 |
| 9 | B | 2 | 10.260 | 10.375 | 30 | 173 | 109 | 14 |
| 10 | C | 2 | 10.260 | 10.375 | 30 | 151 | 108 | 14 |
| 11 | D | 2 | 10.260 | 10.375 | 30 | 306 | 160 | 14 |
| 12 | E | 2 | 10.260 | 10.375 | 30 | 216 | 138 | 14 |
| 13 | F | 2 | 10.260 | 10.375 | 30 | 292 | 160 | 14 |
| 14 | G | 2 | 10.260 | 10.375 | 30 | 127 | 79 | 14 |
| 15 | H | 2 | 10.260 | 10.375 | 30 | 322 | 174 | 14 |
| 16 | I | 2 | 10.260 | 10.375 | 30 | 159 | 65 | 14 |
| 17 | J | 2 | 10.260 | 10.375 | 30 | 234 | 107 | 14 |
| 18 | F | 3 | 10.375 | 10.623 | 30 | 292 | 160 | 14 |
| 19 | G | 3 | 10.375 | 10.623 | 30 | 127 | 79 | 14 |
| 20 | H | 3 | 10.375 | 10.623 | 30 | 322 | 174 | 14 |
| 21 | I | 3 | 10.375 | 10.623 | 30 | 159 | 65 | 14 |
| 22 | J | 3 | 10.375 | 10.623 | 30 | 234 | 107 | 14 |
| 23 | K | 3 | 10.375 | 10.623 | 30 | 260 | 47 | 14 |
| 24 | L | 3 | 10.375 | 10.623 | 30 | 219 | 109 | 14 |
| 25 | M | 3 | 10.375 | 10.623 | 30 | 234 | 107 | 14 |
| 26 | N | 3 | 10.375 | 10.623 | 30 | 181 | 153 | 14 |
| 27 | O | 3 | 10.375 | 10.623 | 30 | 88 | 62 | 14 |
| 28 | L | 4 | 10.623 | 10.809 | 43 | 219 | 109 | 20.5 |
| 29 | M | 4 | 10.623 | 10.809 | 43 | 234 | 107 | 20.5 |
| 30 | N | 4 | 10.623 | 10.809 | 43 | 181 | 153 | 20.5 |
| 31 | O | 4 | 10.623 | 10.809 | 43 | 88 | 62 | 20.5 |
| 32 | P | 4 | 10.623 | 10.809 | 43 | 284 | 177 | 20.5 |
| 33 | Q | 4 | 10.623 | 10.809 | 43 | 206 | 124 | 20.5 |
| 34 | R | 4 | 10.623 | 10.809 | 42 | 87 | 62 | 20 |
| 35 | O | 5 | 10.809 | 11.458 | 50 | 88 | 62 | 24 |
| 36 | P | 5 | 10.809 | 11.458 | 50 | 284 | 177 | 24 |
| 37 | Q | 5 | 10.809 | 11.458 | 50 | 206 | 124 | 24 |
| 38 | R | 5 | 10.809 | 11.458 | 50 | 87 | 62 | 24 |
| 39 | S | 5 | 10.809 | 11.458 | 50 | 201 | 138 | 24 |
| 40 | T | 5 | 10.809 | 11.458 | 50 | 220 | 93 | 24 |
| 41 | U | 6 | 11.458 | 12.058 | 300 | 250 | 150 | 149 |

Fig. 12

| No | COMPOUND NAME | SEGMENT | MEASUREMENT START TIME (min) | MEASUREMENT END TIME (min) | EVENT TIME (msec) | MEASUREMENT TARGET ION m/z 1 | MEASUREMENT TARGET ION m/z 2 | DWELL TIME (msec) |
|---|---|---|---|---|---|---|---|---|
| 1 | A | 1 | 10.000 | 10.550 | 24 | 127 | 79 | 11.0 |
| 2 | B | 1 | 10.000 | 10.550 | 23 | 173 | 109 | 10.5 |
| 3 | C | 1 | 10.000 | 10.550 | 23 | 151 | 108 | 10.5 |
| 4 | D | 1 | 10.000 | 10.550 | 23 | 306 | 160 | 10.5 |
| 5 | E | 1 | 10.000 | 10.550 | 23 | 216 | 138 | 10.5 |
| 6 | F | 1 | 10.000 | 10.550 | 23 | 292 | 160 | 10.5 |
| 7 | G | 1 | 10.000 | 10.550 | 23 | 127 | 79 | 10.5 |
| 8 | H | 1 | 10.000 | 10.550 | 23 | 322 | 174 | 10.5 |
| 9 | I | 1 | 10.000 | 10.550 | 23 | 159 | 65 | 10.5 |
| 10 | J | 1 | 10.000 | 10.550 | 23 | 234 | 107 | 10.5 |
| 11 | K | 1 | 10.000 | 10.550 | 23 | 260 | 47 | 10.5 |
| 12 | L | 1 | 10.000 | 10.550 | 23 | 219 | 109 | 10.5 |
| 13 | M | 1 | 10.000 | 10.550 | 23 | 234 | 107 | 10.5 |
| 14 | J | 2 | 10.550 | 11.458 | 28 | 234 | 107 | 13.0 |
| 15 | K | 2 | 10.550 | 11.458 | 28 | 260 | 47 | 13.0 |
| 16 | L | 2 | 10.550 | 11.458 | 28 | 219 | 109 | 13.0 |
| 17 | M | 2 | 10.550 | 11.458 | 27 | 234 | 107 | 12.5 |
| 18 | N | 2 | 10.550 | 11.458 | 27 | 181 | 153 | 12.5 |
| 19 | O | 2 | 10.550 | 11.458 | 27 | 88 | 62 | 12.5 |
| 20 | P | 2 | 10.550 | 11.458 | 27 | 284 | 177 | 12.5 |
| 21 | Q | 2 | 10.550 | 11.458 | 27 | 206 | 124 | 12.5 |
| 22 | R | 2 | 10.550 | 11.458 | 27 | 87 | 62 | 12.5 |
| 23 | S | 2 | 10.550 | 11.458 | 27 | 201 | 138 | 12.5 |
| 24 | T | 2 | 10.550 | 11.458 | 27 | 220 | 93 | 12.5 |
| 25 | U | 3 | 11.458 | 12.058 | 300 | 250 | 150 | 298 |

Fig. 13

| No | COMPOUND NAME | RETENTION TIME (mm) | PROCESS TIME (mm) | QUANTITATIVE ION m/z-1 | CONFIRMATION ION m/z-2 |
|----|---------------|---------------------|-------------------|------------------------|------------------------|
| 1  | A | 10.222 | ±0.1 | 79  | 127 |
| 2  | B | 10.254 | ±0.1 | 109 | 173 |
| 3  | C | 10.255 | ±0.1 | 108 | 151 |
| 4  | D | 10.256 | ±0.1 | 160 | 306 |
| 5  | E | 10.264 | ±0.1 | 138 | 216 |
| 6  | F | 10.296 | ±0.1 | 160 | 292 |
| 7  | G | 10.349 | ±0.1 | 79  | 127 |
| 8  | H | 10.369 | ±0.1 | 174 | 322 |
| 9  | I | 10.380 | ±0.1 | 65  | 159 |
| 10 | J | 10.462 | ±0.1 | 107 | 234 |
| 11 | K | 10.483 | ±0.1 | 47  | 260 |
| 12 | L | 10.607 | ±0.1 | 109 | 219 |
| 13 | M | 10.638 | ±0.1 | 107 | 234 |
| 14 | N | 10.700 | ±0.1 | 153 | 181 |
| 15 | O | 10.710 | ±0.1 | 62  | 88  |
| 16 | P | 10.762 | ±0.1 | 177 | 284 |
| 17 | Q | 10.855 | ±0.1 | 124 | 206 |
| 18 | R | 10.866 | ±0.1 | 62  | 87  |
| 19 | S | 10.938 | ±0.1 | 138 | 201 |
| 20 | T | 10.958 | ±0.1 | 93  | 220 |
| 21 | U | 11.958 | ±0.1 | 150 | 250 |

Fig. 16

| No | COMPOUND NAME | SEGMENT | MEASUREMENT START TIME (min) | MEASUREMENT END TIME (min) | EVENT TIME (msec) | MEASUREMENT TARGET ION m/z-1 | MEASUREMENT TARGET ION m/z-2 | DWELL TIME (msec) |
|---|---|---|---|---|---|---|---|---|
| 1 | A | 1 | 10.000 | 11.458 | 15 | 127 | 79 | 6.5 |
| 2 | B | 1 | 10.000 | 11.458 | 15 | 173 | 109 | 6.5 |
| 3 | C | 1 | 10.000 | 11.458 | 15 | 151 | 108 | 6.5 |
| 4 | D | 1 | 10.000 | 11.458 | 15 | 306 | 160 | 6.5 |
| 5 | E | 1 | 10.000 | 11.458 | 15 | 216 | 138 | 6.5 |
| 6 | F | 1 | 10.000 | 11.458 | 15 | 292 | 160 | 6.5 |
| 7 | G | 1 | 10.000 | 11.458 | 15 | 127 | 79 | 6.5 |
| 8 | H | 1 | 10.000 | 11.458 | 15 | 322 | 174 | 6.5 |
| 9 | I | 1 | 10.000 | 11.458 | 15 | 159 | 65 | 6.5 |
| 10 | J | 1 | 10.000 | 11.458 | 15 | 234 | 107 | 6.5 |
| 11 | K | 1 | 10.000 | 11.458 | 15 | 260 | 47 | 6.5 |
| 12 | L | 1 | 10.000 | 11.458 | 15 | 219 | 109 | 6.5 |
| 13 | M | 1 | 10.000 | 11.458 | 15 | 234 | 107 | 6.5 |
| 14 | N | 1 | 10.000 | 11.458 | 15 | 181 | 153 | 6.5 |
| 15 | O | 1 | 10.000 | 11.458 | 15 | 88 | 62 | 6.5 |
| 16 | P | 1 | 10.000 | 11.458 | 15 | 284 | 177 | 6.5 |
| 17 | Q | 1 | 10.000 | 11.458 | 15 | 206 | 124 | 6.5 |
| 18 | R | 1 | 10.000 | 11.458 | 15 | 87 | 62 | 6.5 |
| 19 | S | 1 | 10.000 | 11.458 | 15 | 201 | 138 | 6.5 |
| 20 | T | 1 | 10.000 | 11.458 | 15 | 220 | 93 | 6.5 |
| 21 | U | 2 | 11.458 | 12.058 | 300 | 250 | 150 | 298 |

CHROMATOGRAPH MASS SPECTROMETER

CROSS REFERENCE TO RELATED APPLICATIONS

This application is a National Stage of International Application No. PCT/JP2012/075054 filed Sep. 28, 2012, the contents of which are incorporated herein by reference in their entirety.

TECHNICAL FIELD

The present invention relates to a chromatograph mass spectrometer including a combination of a chromatograph and a mass spectrometer unit, such as a gas chromatograph mass spectrometer (GC/MS) or a liquid chromatograph mass spectrometer (LC/MS). More specifically, the present invention relates to a chromatograph mass spectrometer which performs measurements, such as selected ion monitoring (SIM) measurement or multiple reaction monitoring (MRM) measurement (also called "selection reaction monitoring (SRM)" measurement), for known compounds in a mass spectrometer.

BACKGROUND ART

Chromatograph mass spectrometers including a combination of a chromatograph, such as a gas chromatograph (GC) or a liquid chromatograph (LC), and a mass spectrometer, such as a quadrupole mass spectrometer, are widely used to perform qualitative or quantitative analyses of various components contained in a sample. When a quantitative analysis of known compounds is performed using a chromatograph mass spectrometer, an SIM measurement method is typically used which selectively and repeatedly detects only ions having a specific mass-to-charge ratio m/z or ions including specific mass-to-charge ratios m/z which are previously designated.

When a known compound is quantitatively analyzed using a chromatograph mass spectrometer including a combination of a chromatograph, such as GC or LC, and a triple quadrupole mass spectrometer, an MRM measurement method is used. According to this method, an ion (precursor ion) having a specific mass-to-charge ratio is selected at a first-stage quadrupole mass filter, the ion is dissociated by collision-induced dissociation (CID) in a collision cell, and an ion having a specific mass-to-charge ratio among resultantly generated product ions is selected and detected by a second-stage quadrupole mass filter. The MRM measurement method can remove deleterious effects of irrelevant components through the two-stage quadrupole mass filter. Accordingly, this method has an advantage of improving the S/N ratio and achieving highly sensitive quantitative measurement.

In any case of performing quantitative analysis through SIM measurement or MRM measurement using a chromatograph mass spectrometer, the value of mass-to-charge ratios corresponding to target compounds are required to be set in conformity with the retention times of the target compounds as one measurement condition. For example, chromatograph mass spectrometers described in Patent Literatures 1 and 2 have a function of automatically creating a parameter table representing a measurement condition. After an analysis operator previously creates a compound table including information on measurement target compounds, the parameter table is automatically created based on the information described in the compound table. Such a function of automatically creating a parameter table according to a conventional chromatograph mass spectrometer will be described with reference to a specific example.

FIG. 13 is an example of a compound table. As shown in the diagram, the compound table includes information including the compound name, the predicted retention time, the process time, the mass-to-charge ratio of a quantitative ion, and the mass-to-charge ratio of a confirmation ion for each compound. The quantitative ion is an ion which best characterizes the compound. The confirmation ion is an ion which has another mass-to-charge ratio different from that of the quantitative ion and characterizes the compound. This confirmation ion is typically used to confirm that the chromatogram peak of the quantitative ion originates from the target compound by using the relative ratio between the signal intensity of the confirmation ion peak and the signal intensity of the quantitative ion peak on the mass spectrum. The retention time is the predicted value of the time of elution from a column in the liquid chromatograph. The process time is a parameter for designating a time range during which the compound is measured, where an appropriate time margin is set centering the predicted retention time so as to accommodate the variation in peak width and retention time. Accordingly, even if the retention time of a compound varies, the peak of the compound reliably appears within a range of the retention time of the compound±the process time. FIG. 14 shows the relationship between the peak of a compound on a chromatogram and retention time and process time.

In the process of automatically creating the parameter table according to a measurement method, a measurement time is appropriately divided into segments based on the compound table as described above. A segment is a smallest time unit for setting a measurement condition, such as a condition of target ion or the polarity of target ion to be measured. The measurement condition can be switched on a segment-by-segment basis.

In the conventional process of automatically creating a parameter table, a boundary between segments is automatically set at a time point within an interval between retention times of compounds to be measured is sufficiently large. More specifically, if a conditional expression,

[the retention time of a compound $X+A$]<[the retention time of the compound $X+1$ having the next longer retention time$-A$](where $A$ is a process time)     (1)

is satisfied, the segment boundary is set at a time point where the elution time range (retention time$\pm A$) of the compound X does not overlap with the elution time range of the compound X+1, typically at an intermediate time point between the retention time for the compound X and the retention time for the compound X+1, and thus the measurement time is divided into different segments by the segment boundary.

FIG. 15A and FIG. 15B show chromatograms illustrating a segment dividing method. As shown in FIG. 15A, if the elution time ranges of the compound X and the compound X+1 overlap with each other, no segment boundary is set. That is to say, in this case, the compound X and the compound X+1 belong to the same segment. Meanwhile, as shown in FIG. 15B, if the elution time ranges of the compound X and the compound X+1 do not overlap with each other, a segment boundary is determined between the retention time of the compound X and the retention time of the compound X+1. Thus, the compound X and the compound X+1 belong to different segments. According to such_ an algorithm, segments can be defined for all the compounds (or some compounds designated by an analysis operator) listed in the compound table.

FIG. 16 shows one example of a parameter table of a measurement method automatically created based on the compound table shown in FIG. 13. In the parameter table, the measurement condition for one compound is listed as a "measurement event" on one row. Each measurement event lists, besides the compound name, the number of a segment where the compound is measured (hereinafter, the segment number is indicated by "#"), the measurement start time, the measurement end time, the event time, the mass-to-charge ratio of the ion to be measured, and the dwell time. In the mass-to-charge ratio of the ion to be measured, the mass-to-charge ratio m/z-1 of the quantitative ion and the mass-to-charge ratio m/z-2 of the confirmation ion of the compound to be measured are set. The measurement start time and the measurement end time are the start time and the end time of the segment. The event time is a unit time of repetition of the measurement event. The dwell time is the time during which the detector actually receives and accumulates ions, that is, data collection time.

In the example in FIG. 13 and FIG. 16, a time interval sufficiently satisfying the conditional expression (1) exists between a compound T and a compound U having the next longer retention time. Accordingly, a segment boundary is set there. Segment #1 and segment #2 are created before and after the boundary. Compounds A to T are assigned to be measured in the time period of segment #1 whose measurement start time is 10.000 [min] and measurement end time is 11.458 [min]. FIG. 5 is a schematic diagram showing the relationship of segments and compounds with time as abscissa.

The event time is automatically calculated from a preset measurement point time interval, which is called a loop time, and the number of compounds measured in one segment. FIG. 16 shows an example where the loop time is set to 300 [msec]. The ions originating from each compound need to be measured at an interval of a loop time of 300 [msec]. Since the number of compounds to be measured in segment #1 is 20, the event time allotted to each compound is 300 [msec]/20=15 [msec]. Meanwhile, in segment #2, the compound to be measured is the compound U alone, and the same loop time 300 [msec] is allotted as the event time.

As described above, the dwell time is the time during which the detector actually captures ions. The event time includes, in addition to the dwell time, wait time (hereinafter, called "voltage stabilization wait time") for stabilizing the voltage after the voltage applied to a quadrupole mass filter is changed. The dwell time also depends on the number of ions to be measured in one event time. Accordingly, the dwell time Td for each ion is calculated by the following equation (2).

$$Td=(\text{event time}-\text{voltage stabilization wait time})/[\text{the number of ions to be measured}] \quad (2)$$

In the example of FIG. 16, the voltage stabilization wait time per ion to be measured is set to 1 [msec]. As a result, the dwell time Td for each ion is $(15-1\times2)/2=6.5$ [msec]

If the dwell time is too short, unfavorable effects of external factors, such as drift and noise, tend to be included in signal intensity data acquired by the detector, making it difficult to achieve sufficient measurement reproducibility. Accordingly, accurate quantitative measurement requires an adequate length of dwell time. To secure an adequate dwell time, the event time is required to be long. And it is preferred to increase the number of segments to reduce the number of compounds to be measured allotted to one segment. However, the aforementioned conventional algorithm of automatically creating a parameter table cannot finely set segments, and many compounds are allotted to one segment, if there are many compounds having retention time close to each other. As a result, the dwell time for each ion is necessarily shortened, which may incur reduction of the accuracy of quantitative measurement because sufficient measurement reproducibility and measurement sensitivity cannot be achieved. According to the example in FIG. 13 and FIG. 16, the compounds A to T are allotted to one segment, which resultantly reduces the dwell time.

On the other hand, to secure a long dwell time, an analysis operator (user) can finely divide segments through manual operation. However, if segments are just finely divided, a part of elution time range defined by retention time±A of some compounds may trespass the segment boundary, and data cannot be collected in the part of the elution time range. In such a case, if the retention time of the compound changes owing to an influence of a minor component or the like (i.e., if the peak position shifts as indicated by broken lines in FIG. 14), a part of the peak corresponding to the compound on the chromatogram is eclipsed and the peak area cannot be accurately measured. Accordingly, quantitative accuracy is substantially reduced.

It is possible to set a long loop time to secure long dwell time. However, if the loop time is set long, the measurement time interval elongates, and the number of data points constituting one peak is reduced. As a result, the peak top cannot be correctly determined, and the shape of curve is not adequately detected at the rising part and the falling part of the peak. The problems reduce the detection accuracy of the peak area, and deteriorates the quantitative measurement.

CITATION LIST

Patent Literature

[Patent Literature 1] JP 2003-172726 A
[Patent Literature 2] JP 2012-132799 A

SUMMARY OF INVENTION

Technical Problem

The present invention aimed at solving the previously described problems has an object to provide a chromatograph mass spectrometer which can perform highly accurate quantitative analysis by appropriately setting segments such that the dwell time, the loop time, and the elution time range centering the retention time for each of ions originating from every compound to be measured satisfy required values as much as possible.

Solution to Problem

The present invention made in order to solve the problems is a chromatograph mass spectrometer including a combination of a chromatograph for temporally separating compounds in a sample and a mass spectrometer unit for separating ions originating from the compounds separated by the chromatograph according to mass-to-charge ratios and detecting the ions, the mass spectrometer unit performing selected ion monitoring (SIM) measurement or multiple reaction monitoring (MRM) measurement for one or more specific mass-to-charge ratios at around a chromatogram peak corresponding to a target compound, the chromatograph mass spectrometer including:

a) a compound table holding unit which stores a compound table including at least information identifying an estimated retention time or an the estimated elution time range and one or more mass-to-charge ratios to be measured, for each of compounds to be measured; and b) a measurement condition information creating unit which creates a measurement condition table including at least information identifying an actual measurement start time, an actual measurement end time and a mass-to-charge ratio to be measured, for each of the compounds to be measured listed in the compound table, based on the information included in the compound table, in order to perform SIM measurement or MRM measurement, wherein the measurement condition information creating unit includes:

b1) a primary segment setting unit which determines a boundary at a time point where the elution time ranges of the compounds included in the compound table do not overlap with each other to set segments each of which is a measurement time unit, and assign one or more compounds to be measured to each segment;

b2) a primary determination unit which, for each of the segments set by the primary segment setting unit, calculates a dwell time, which is data collection time per ion originating from one compound, based on the number of compounds assigned to each segment, loop time which is a previously given measurement point time interval for each ion and the number of ions to be measured for one compound, and determines whether the dwell time is shorter than a previously given dwell time minimum value or not; and b3) a segment dividing process unit which, if the primary determination unit determines that the dwell time calculated for a segment is shorter than the previously given dwell time minimum value, performs segment subdivision and compound reassignment by forcedly dividing one segment into a plurality of segments such that the dwell time is equal to or longer than the minimum value, and arranging a compound having an elution time range trespassing a newly defined segment boundary to be measured in both segments across the segment boundary.

In the present invention, the "elution time range" of a compound is a time range set so as to secure a certain time width defined in consideration of the peak width and positional variation of the peak around the estimated retention time of the compound. The time width depends on a margin appropriately considered. Accordingly, the time width may be previously defined as a default, or alternatively, an analysis operator may be allowed to input and set the time width. In case the time width is defined as a default, the elution time range is uniquely determined according to the retention time, so that the elution time ranges can be defined for each of the compounds in the compound table. If only the retention times are defined for the compounds in the compound table, the elution time ranges of the compounds can be calculated based on the retention times and default or externally given time widths. The "loop time which is a previously given measurement point time interval" and "previously given dwell time minimum value" may also be defined as defaults. Alternatively, the analysis operator may be allowed to input and set these items.

In the chromatograph mass spectrometer according to the present invention, the primary segment setting unit determines a boundary at a time point where the elution time ranges for the compounds included in the compound table do not overlap with each other to thereby set segments, and assign one or more compounds to be measured to each segment. In this case, the elution time range of one compound does not trespass the segment boundary, and one compound is assigned to only one segment. If many compounds have retention times close to each other, many compounds are assigned to one segment. On the contrary, if there is no compound having close retention times, only one compound is assigned to one segment.

As described above, the ions originating from each compound are necessarily measured in each measurement time interval defined by the loop time. Thus, if the number of compounds assigned to one segment is large, the measurement time (the event time) allotted to one compound is short, and the dwell time is also short accordingly. The primary determination unit calculates the dwell time based on the number of compounds assigned to the segment, the previously given loop time, and the number of ions to be measured for one compound in each segment. It is then determined whether the calculated dwell time is shorter than the dwell time minimum value or not.

There is no problem in the segments having calculated dwell time no shorter than the dwell time minimum value. However, if the calculated dwell time is shorter than the dwell time minimum value, adequate S/N ratio and sensitivity cannot be achieved through measurement of the ions originating from the compound assigned to the segment. First, the segment dividing process unit forcedly subdivides the segment having the calculated dwell time shorter than the dwell time minimum value into a plurality of segments.

The segment boundary newly determined by segment subdivision does not satisfy the condition for determining the segment boundary by the primary segment setting unit. Accordingly, the elution time range for at least one of compounds assigned to the segment before subdivision trespasses the newly determined segment boundary. The compounds having the elution time range trespassing the newly determined segment boundary are reassigned so as to be measured in both the segments across the segment boundary. In this case, one compound is assigned not only to one segment but also multiple segments temporally adjacent to each other. Accordingly, even in if the position of the peak shifts, eclipse of the peak due to missing of a part of peak data can be prevented.

When a segment is forcedly subdivided into multiple segments and the compounds are reassigned, the number of compounds assigned to the segment is reduced. Accordingly, the dwell time is increased in comparison with that before segment subdivision and compound reassignment, and is likely to become longer than the dwell time minimum value. In general, the larger the number of subdivision of a segment is, the higher the possibility of decreasing the number of compounds per segment, and increasing the dwell time, is. However, even if one segment is forcedly subdivided into multiple segments, it is not assured that the dwell time become larger than the dwell time minimum value.

Preferably, the chromatograph mass spectrometer according to the present invention includes a secondary determination unit which, after subdivision and compound assignment for forcefully subdividing one segment into a plurality of segments, recalculates the dwell time in each segment generated by the subdivision, and determines whether the dwell time is shorter than the previously given dwell time lower limit value or not, and the segment dividing process unit changes the number of divisions or a division point according to which one segment before subdivision and is forcedly subdivided, to newly perform segment subdivision and compound assignment, if the secondary determination unit determines that the recalculated dwell time is shorter than the dwell time lower limit value.

According to this configuration, repetition of determining the dwell time by the secondary determination unit, and segment subdivision and compound assignment by the segment dividing process unit increases the possibility capable of finding an appropriate condition so that a dwell time is no shorter than the dwell time minimum value.

For example, as a method of forcedly subdividing one segment into a plurality of segments, the compounds assigned to the one segment are classified into groups each including a predetermined number of compounds having retention times close to each other, thereby allowing a new segment boundary to be determined. Instead of the number of compounds, for example, the number of divisions may be designated to forcedly subdivide one segment into a plurality of segments; such as divisions of two, three or more.

In the case of defining the number of compounds to be included in one of subdivided segments and performing subdivision, it is preferred to appropriately designate an initial value of the number of compounds first, and then increase or decrease the number of compounds in sequence from the initial value each time of newly segment subdivision and compound reassignment. As described above, there is a tendency that the smaller the number of compounds assigned to one segment, the longer the dwell time is. Accordingly, only if the dwell time is concerned, the large number of divisions is preferred. However, there is generally constraints due to the specification of the system on the total number of segments and the number of rows of the measurement condition table (the cumulative number of compounds assigned to each segment). If the number of segment divisions is too much increased, the constraint condition cannot be satisfied.

Thus, in the chromatograph mass spectrometer according to the present invention, it is preferred that the segment dividing process unit perform segment subdivision and compound reassignment such that the dwell time is no shorter than the dwell time minimum value, and the total number of segments and/or the number of rows of measurement condition table is within a predetermined value.

In the case where the number of compounds having retention times close to each other is significantly large or the case where the setting value of the dwell time minimum value, the loop time or other condition is inappropriate, any possible segment subdivision sometimes cannot satisfy the designated condition. Preferably, the chromatograph mass spectrometer according to the present invention further includes a warning unit of warning to change the designated condition if it is determined that the condition cannot be satisfied or the possibility incapable of satisfying this condition is high. More specifically, for instance, in the case where an analysis operator inputs and sets the dwell time and loop time, it is preferred to display, on a screen, a warning indication indicating that such input and setting is inappropriate.

Advantageous Effects of Invention

The chromatograph mass spectrometer according to the present invention automatically create the parameter table of a measurement method in which dwell times for the ions originating from all the compounds to be measured have equal to or longer than required values without requiring the analysis operator (user) to perform complicated calculation, operation and work, even in the case with many measurement target compounds having retention times close to each other. Accordingly, data can be collected with sufficiently high measurement reproducibility and measurement sensitivity while a load on the analysis operator is reduced, which can improve the accuracy and reproducibility of the quantitative value calculated from a peak area on a chromatogram or the like.

BRIEF DESCRIPTION OF DRAWINGS

FIG. 8 is a diagram showing an example of a parameter table of a measurement method created by executing an automatic segment dividing process in the LC/MS of the first embodiment based on a compound table shown in FIG. 13.

FIG. 12 is a diagram showing an example of a parameter table of a measurement method created by executing an automatic segment dividing process in the LC/MS of the second embodiment based on a compound table shown in FIG. 13.

FIG. 13 is a diagram showing an example of a compound table.

FIG. 16 shows a parameter table of a measurement method created by a conventional function of automatically creating a parameter table based on the compound table shown in FIG. 13.

DESCRIPTION OF EMBODIMENTS

A liquid chromatograph mass spectrometer (LC/MS) according to a first embodiment of the present invention will now be described with reference to the attached drawings.

Figure 1:
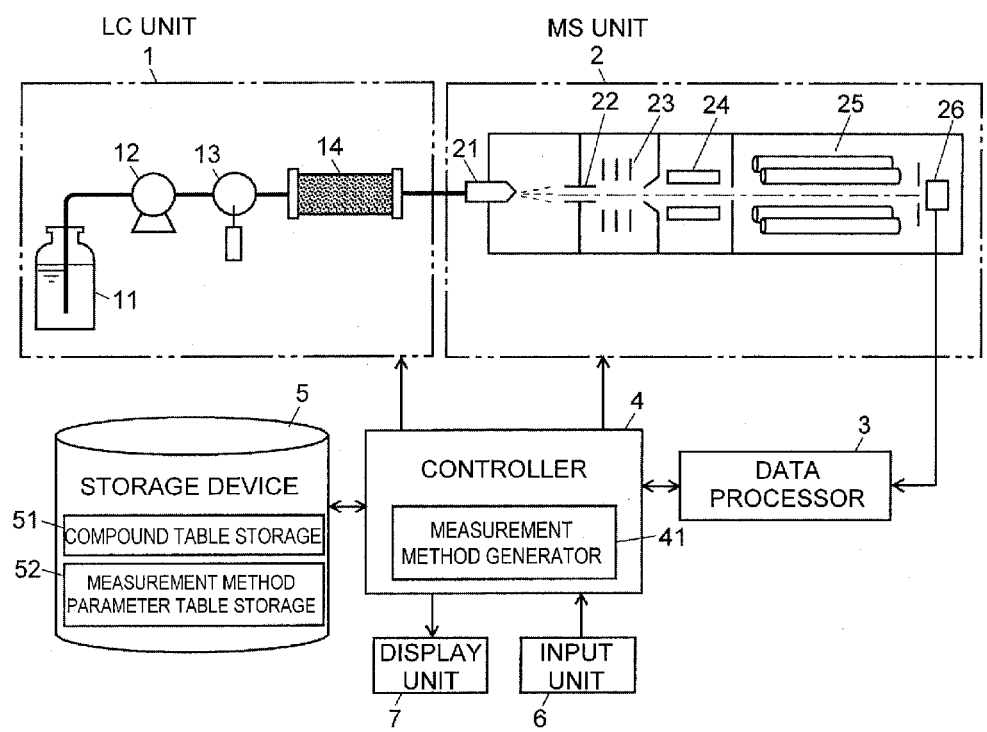
FIG. 1 is a configuration diagram of a main part of an LC/MS of a first embodiment of the present invention.

FIG. 1 is a configuration diagram of a main part of the LC/MS as the first embodiment of the present invention. The LC/MS of this embodiment includes a liquid chromatograph unit (LC unit) 1 for temporally separating various compounds contained in a sample, and a mass spectrometer unit (MS unit) 2 for performing mass spectrometric analysis of the separated various compounds.

The LC unit 1 includes a mobile phase container 11 for storing mobile phase, a liquid transport pump 12 for drawing the mobile phase and transporting it at a constant flow rate, an injector 13 for injecting a sample into the mobile phase at a predetermined timing, and a column 14 for temporally separating various compounds in the sample.

The MS unit 2 includes a spray nozzle 21 for ionizing an elution containing compounds eluted from the column 14 by electrospraying the elute into an atmospheric environment, a heating capillary 22 for guiding the ions originating from the compounds in the sample into a vacuum environment, ion guides 23 and 24 for transporting the ions the subsequent stage while focusing them, a quadrupole mass filter 25 for allowing only ions having a specific mass-to-charge ratio to pass, and a detector 26 for detecting the ions passed through the quadrupole mass filter 25.

A detected signal acquired by the detector 26 of the MS unit 2 is converted into digital values by an A/D converter, not shown, and subsequently input into a data processor 3. The data processor 3 creates a mass spectrum and a chromatogram and performs quantitative analysis by executing a prescribed operation process. A controller 4 controls the operations of the LC unit 1, the MS unit 2, and the data processor 3. The controller 4 includes a measurement method generator 41 which serves as a functional block characterized by the present invention. The controller 4 is connected to a storage device 5 for storing a compound table and a measurement method parameter table, an input unit 6, such as a keyboard and a pointing device, operated by an analysis operator (user), and a display unit 7 for displaying information input and set by the analysis operator and analysis result.

The functions of the data processor 3 and the controller 4 can be achieved by using a personal computer (PC) including a CPU and a memory as hardware, and performing control/processing software previously installed in the PC.

An example of operation of the LC/MS of this embodiment in quantitative analysis of a known compound contained in a sample will be briefly described. In this case, the quadrupole mass filter 25 of the MS unit 2 is driven in an SIM measurement mode so as to selectively pass ions originating from a compound to be quantitatively analyzed (hereinafter, called target compound) and having mass-to-charge ratios.

In a state where the mobile phase is transported by the liquid transport pump 12 into the column 14 at a substantially constant flow rate, the injector 13 injects the sample into the mobile phase. The injected sample is carried by the mobile phase and introduced into the column 14, and various compounds in the sample are temporally separated while passing through the column 14. At around a time point a prescribed time after a prescribed time is elapsed with a sample injected time point as a reference (that is, in proximity to the retention time of a target compound), the target compound is eluded from an output port of the column 14. The target compound thus eluded reaches the spray nozzle 21 of the MS unit 2, and ions originating from the compound are generated. The ions pass through the heating capillary 22 and the ion guides 23 and 24, and then introduced into the quadrupole mass filter 25. The quadrupole mass filter 25 allows only ions originating from the target compound and having specific mass-to-charge ratios to selectively pass. The ions having passed reach the detector 26 which detects the ions. The data processor 3 creates a mass chromatogram (also called an extracted ion chromatogram) which shows the relationship between ion intensities for the specific mass-to-charge ratios and lapses of time, according to data based on a detected signal acquired by the detector 26.

If the sample contains the target compound, a peak appears in and around the retention time of the target compound on the mass chromatogram. Thus, the data processor 3 extracts the peak originating from the target compound on the mass chromatogram, and calculates the peak area value. This processor refers to a calibration curve which indicates the relationship between the peak area value previously created according to a result acquired by measuring a standard sample and the like and the concentration (the amount of content) of the target compound to thereby calculate the concentration of the target compound. If there are a plurality of compounds to be quantitatively analyzed, a mass chromatogram is created based on data acquired by SIM measurement for ions having mass-to-charge ratios different from each other with respect to compounds. The area values of the ion peak originating from the target compound are calculated as described above. The concentration of the target compound is calculated based on the area values.

In the LC/MS of this embodiment, the controller 4 controls the operations of the LC unit 1, the MS unit 2 and the data processor 3 according to the parameter table stored in the measurement method parameter table storage 52 in the storage device 5. In the case of quantitating a plurality of compounds contained in the sample with single sample injection such as multi-component simultaneous analysis, creation of a parameter table by the analysis operator himself/herself is significantly complicated and often causes errors. For addressing the above, the controller 4 includes the measurement method generator 41 for automatically creating a parameter table using a compound table. The measurement method generator 41 has characteristic functions different from those of conventional parameter table automatic creation.

A characteristic process of creating a measurement method parameter table, in particular, a characteristic automatic segment dividing process, which is to be executed mainly by the measurement method generator 41 will now be described.

Figure 3:
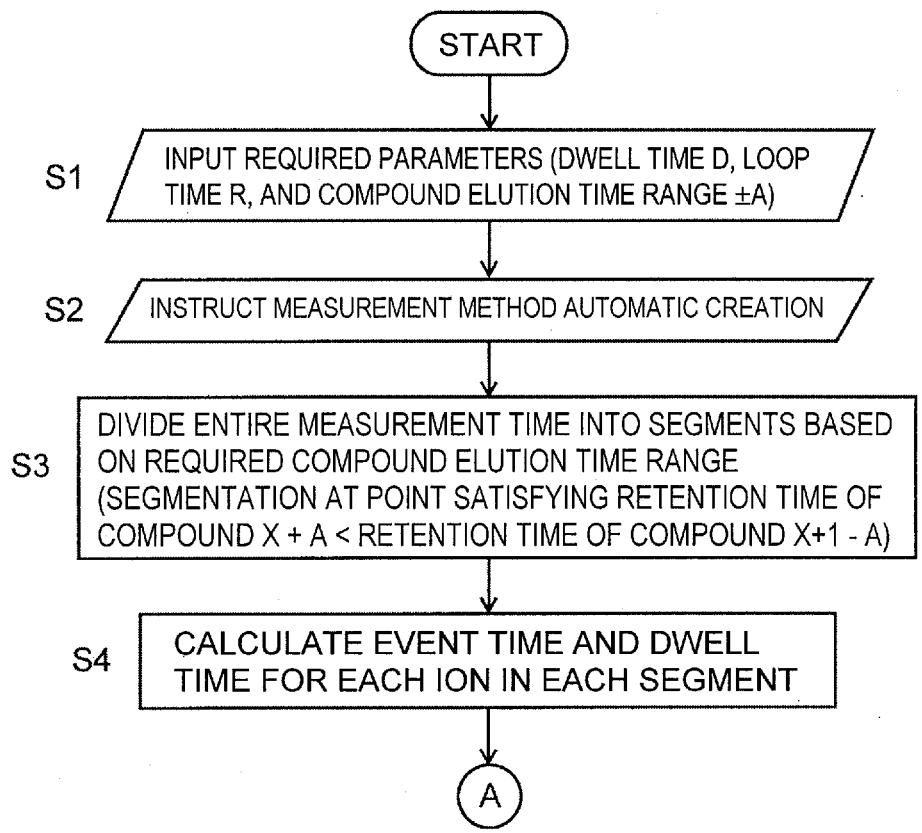
FIG. 3 is a flowchart upon execution of an automatic segment dividing process in the LC/MS of the first embodiment (first part).
Figure 4:
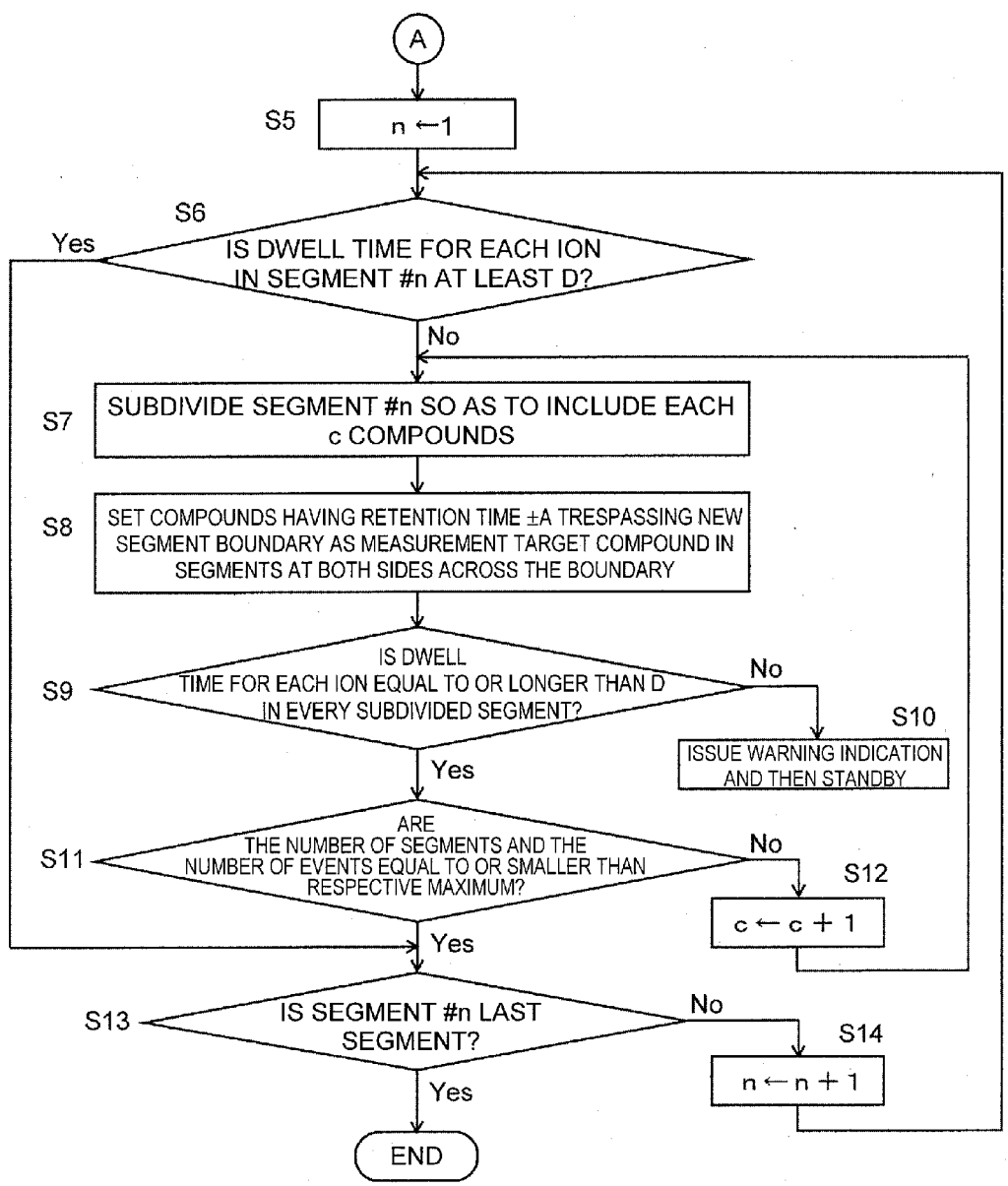
FIG. 4 is a flowchart upon execution of the automatic segment dividing process in the LC/MS of the first embodiment (latter part).

FIG. 3 and FIG. 4 are flowcharts upon the automatic segment dividing process which is characteristic in the process of creating a measurement method parameter table. Description is herein given of the exemplary case where the compound table shown in FIG. 13 is previously stored in the compound table storage 51, and the parameter table is automatically created based on the compound table as a processing target.

Figure 2:
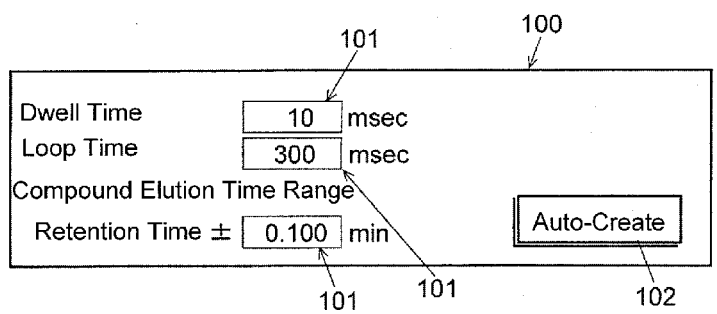
FIG. 2 is a diagram showing an example of an input setting screen on the LC/MS of the first embodiment.

In advance of the process of creating a measurement method parameter table, the analysis operator sets, through the input unit 6, a dwell time minimum value D, loop time R, process time±A and the like as measurement conditions (step S1). More specifically, when the analysis operator performs a predetermined operation through the input unit 6, an input setting screen 100 as shown in FIG. 2 is displayed on the screen of the display unit 7. The analysis operator then inputs appropriate numerical values in text input fields 101. In this example, the dwell time D is 10 [msec], the loop time R is 300 [msec], and the process time±A is ±0.1 [min]. The dwell time D is the dwell time minimum value, and hereinafter referred to as the dwell time lower limit value D.

When the analysis operator instructs execution of a process of automatically creating a measurement method by clicking an "Auto-Create" button 102 in a state after completing the input setting (step S2). In response to the instruction, the measurement method generator 41 reads the designated compound table from the compound table storage 51, and sets segments in which the entire or a part of measurement time is appropriately divided in a manner similar to that of the conventional technique, based on the retention time of each compound and the set process time which are listed in the compound table (step S3). More specifically, two compounds having adjacent retention times which satisfy the conditional expression indicated by the expression (1) are retrieved, the time is separated at the intermediate point of the retention times of the two compounds as the segment boundary. As described above, in the compound table shown in FIG. 13, the two compounds which are the compound T and the compound U satisfy the conditional expression (1). Accordingly, the segment boundary is set at the intermediate point 11.458 (min) between the retention times of the compounds T and U. The former part of the boundary is called a segment #1, and the following part is called a segment #2. The relationship between the segments and compounds at this time is as shown in above-referenced FIG. 5. The process of step S3 corresponds to a process by a primary segment setting unit in the present invention.

Next, in the state where primary segment division is performed as described above, the event time and dwell time are calculated in each segment (step S4). The event time is acquired by dividing the loop time R input and set in step S1 by the number of compounds assigned to the segment. For example, in FIG. 5, 20 compounds are assigned to the segment #1. Accordingly, the event time is 300 [msec]/20=15 [msec]. The two ions (quantitative ion m/z-1 and confirmation ion m/z-2)) are to be measured for one compound. Accordingly, provided that the voltage stabilization wait time is 1 [msec], the dwell time for each ion is (15−2)/2=6.5 [msec]. Meanwhile, only one compound is allotted to the segment #2. Accordingly, the event time is 300 [msec]/1=300 [msec]. The dwell time for each ion is (300−2)/2=149 [msec].

Next, the measurement method generator 41 sets a variable n to one (step S5), and determines whether or not the dwell time in the segment #n calculated in step S4 is equal to or longer than the dwell time minimum value D input and set in step S1 (step S6). If the dwell time in the segment #n is equal to or longer than the dwell time minimum value D, the processing proceeds from step S6 to step S13 without executing the processes in steps S7 to S12, which are segment subdividing processes, for this segment. When step S6 is executed at the first time after step S5, n=1. Accordingly, it is determined whether the dwell time is equal to or longer than the dwell time minimum value or not in the segment #1. The process of step S6 corresponds to a process by a primary determination unit in the present invention.

If it is determined to be No in step S6, the dwell time in the segment #n does not satisfy the requirement of the dwell time lower limit value. Accordingly, an approach of subdivision is made to the segment in order to increase the dwell time. In the example in FIG. 5, the dwell time in the segment #1 is 6.5 [msec] as described above. The time is thus shorter than the dwell time minimum value D=10.0 [msec]. Accordingly, in the case of n=1, the processing proceeds from step S6 to step S7. In step S7, one segment #n is forcedly subdivided into segments each including "c" number of compounds in an ascending order of the retention time for all compounds assigned to the segment #n. Here, the initial value of "c" may be "1". However, in general, c=1 is often too small to satisfy the condition of the total number of segments, which will be described later. Accordingly, it is preferred that the initial value of "c" be about 2 to 5. Here, as an example, the initial value of "c" is set as "4".

Figure 5:
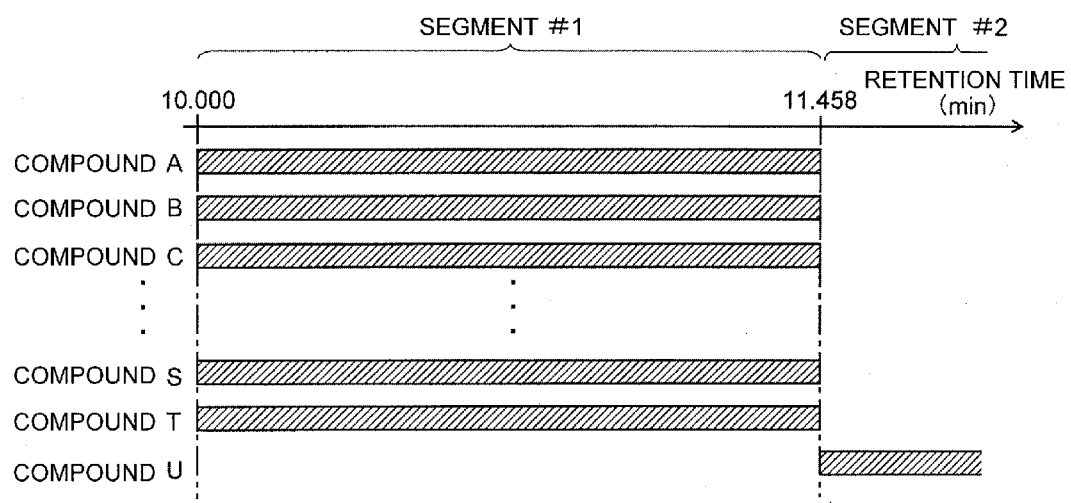
FIG. 5 is a schematic diagram showing an example of a correspondent relationship between segments and compounds primarily created from the compound table shown in FIG. 13 according to a process of automatically dividing segments in the LC/MS of the first embodiment.
Figure 6:
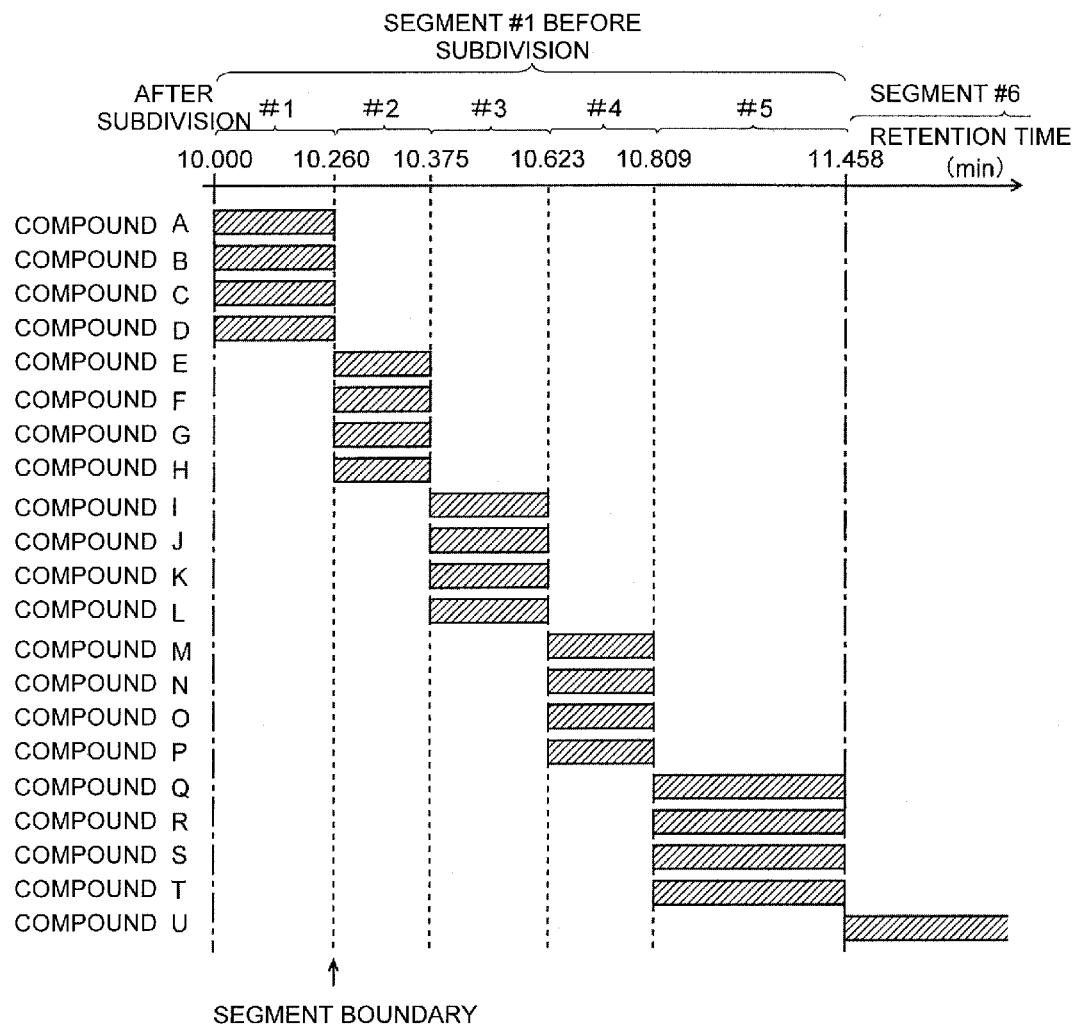
FIG. 6 is a schematic diagram showing one example of the correspondent relationship between segments into which a segment #1 in FIG. 5 is subdivided and compounds.

That is, in the example in FIG. 5, total 20 compounds A to T are assigned to the segment #1. Accordingly, each four compounds is grouped in an ascending order of the retention time to determine a new segment boundary, and the segment #1 is subdivided. As a result, as shown in FIG. 6, one segment #1 before subdivision is subdivided into five. Different four compounds are assigned to each of the new segments. The segment boundary may be set at an intermediate time in the retention times for the subsequent and following compounds.

Although the number of compounds assigned to one segment is decreased due to the process of step 7, since the segment boundary is forcedly set, the elution time ranges of some compounds trespass the segment boundaries. For example, the elution time range of the compound A is 10.222±0.1 [min] (i.e., 10.122 to 10.322 [min]), and its elution time range trespasses the boundary between the segments #1 and #2 because of the boundary 10.260 [min] between the segments #1 and #2 generated by the subdivision. Therefore, as shown in FIG. 5, measurement of the compound A only in the subdivided segment #1 can suffer a loss of the peak (latter part) of the compound A in the case where the position of the peak is deviated. Thus, the assignment of the compound which has the elution time range of the retention time±A trespassing the newly set segment boundary is adjusted so that the compound is measured in both segments across the boundary (step S8).

Figure 7:
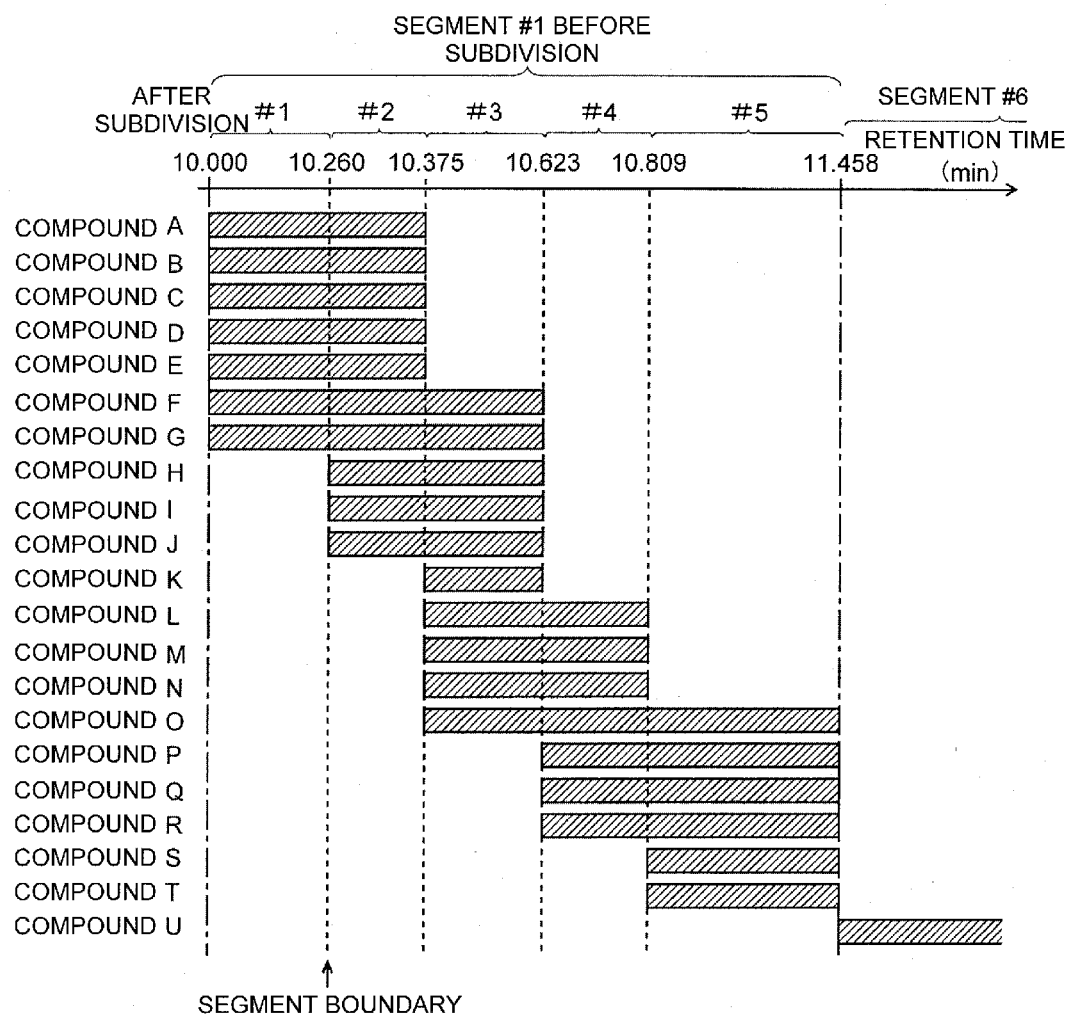
FIG. 7 is a schematic diagram showing an example of the correspondent relationship between segments and compounds after assignment of compounds of which elution time ranges extend over the segment boundary to the segments is adjusted with respect to the segments after reassignment shown in FIG. 6.

For example, the elution time range of the aforementioned compound A trespasses the newly created boundary between the segments #1 and #2. Accordingly, the compound A is assigned not only to the segment #1 but also to the segment #2. The elution time ranges of the compounds F and G trespass not only the newly generated boundary between the segments #1 and #2 but also the newly generated boundary between the segments #2 and #3. Accordingly, the compounds F and G are assigned to three segments #1 to #3. For the example in FIG. 6, such compound reassignment is performed to all the compounds included in the segment #1 before subdivision, and the relationship between the segments and compounds is acquired as shown in FIG. 7. Naturally, subdivision of compounds increases the number of compounds assigned to one segment (e.g., in the example in FIG. 6 and FIG. 7, the number of compounds increases from four to seven in the new segment #1). However, even if the position of the peak deviates, the peak can be reproduced without lack. Accordingly, the quantitativeness is not reduced.

Next, for each of all the segments newly generated by subdividing the segment #n, it is determined whether each calculated dwell time is equal to or longer than the dwell time minimum value or not (step S9). For the example in FIG. 7, the number of compounds assigned to the segment #1 is seven. Accordingly, the event time is 300 [msec]/7=42 [msec]. Two ions are to be measured for one compound. Accordingly, the dwell time for each ion is (42−2)/2=20 [msec]. Furthermore, the number of compounds assigned to the new segment #2 is 10. Accordingly, the event time is 300 [msec]/10=30 [msec] and the dwell time is (30−2)/2=14 [msec]. In all the segments, including the remaining segments, newly generated from the segment #1 before subdivision, the dwell time is equal to or longer than the dwell time minimum value. Accordingly, the processing proceeds from step S9 to step S11.

Next, the total number of segments and the total number of events at this time are calculated, and it is determined whether the numbers are equal to or smaller than the maximum value of the number of segments and maximum value of the number of events, respectively, which are previously set in the spectrometer (step S11). In this example, the maximum value of the number of segments is 128, and the maximum value of the number of events is 512. These values are based on the constraint according to the specification of the system. Accordingly, the maximums are different for each system. If the total number of segments and the total number of events are greater than the maximum value of the number of segments and the maximum value of the number of events, such measurement cannot be achieved even when the dwell time is equal to or longer than the dwell time minimum value. If it is determined to be No in step S11, the parameter "c" of the number of compounds for segment subdivision is incremented by one (step S12), the processing is returned to step S7 and then subdivision of the segment #n and reassignment of compounds are performed. As the value of "c" is incremented, the number of segment divisions is typically reduced. There is thus possibility that the dwell time is reduced, while the total number of segments and the total number of events are reduced. As "c" is sequentially increased, a state can thus be found where the total number of segments and the total number of events fall within the maximum value of the number of segments and the maximum value of the number of events while the dwell time is maintained at the value equal to or longer than the dwell time minimum value.

In the example in FIG. 7, the total number of segments is six and the total number of events is 7+10+10+7+6+1=41 in step S11 at the first time of step S11. Accordingly, in step S11, it is determined to be Yes, and the processing proceeds to step S13. In step S13, it is determined whether the segment #n before subdivision is the last segment or not. If the segment is not the last segment, the variable n is incremented (step S13) and the processing is returned to step S6. Accordingly, the process is time-sequentially performed for all the segments set in step S3. At the last segment, it is determined to be Yes in step S13, and the processing terminates.

After the process of subdividing the segment #1 where n=1 and compound reassignment terminates as described above and the processing proceeds step S13, the segment #1 is not the last segment and therefore the value is incremented n=2 and the processing returns to step S6. Since in the segment #2 having not been subdivided the dwell time is much longer than the dwell time minimum value, the processing proceeds from step S6 to step S13. In step S13, it is determined to be Yes, and all the processes terminate.

According to the algorithm in this embodiment, in the case of increasing the value of "c" in step S12 and repeating segment subdivision and compound reassignment, the dwell time may be shortened but cannot be expected to be long. That is to say, the dwell time where the "c" is the initial value is the longest. Accordingly, if it is determined to be No in step S9, any parameter where the dwell time is equal to or longer than the dwell time minimum value cannot be found. Accordingly, a warning display is output on the screen of the display unit 7, and the state is brought into a standby state (step S10). The analysis operator watching this indication returns the screen to, for example, the input setting screen 100 shown in FIG. 2 and performs an appropriate process, such as for example changing the dwell time minimum value, and instructs parameter table automatic creation again, or instructs as to whether the parameter table automatic creation is continued a result of accepting some segments have dwell time shorter than the dwell time minimum value. If the analysis operator instructs the latter, the processing proceeds step S11 and is continued. That is to say, in this case, the dwell time minimum value is not satisfied, but parameter table automatic creation where the dwell time is set long as much as possible can be attempted.

FIG. 8 shows one example of a parameter table of a measurement method automatically created based on the compound table shown in FIG. 13. As will be understood in comparison with the parameter table shown in FIG. 16, the dwell time is maintained at the time equal to or longer than 10 [msec] for all the compounds A to U, and the peak area can be calculated based on data having a sufficiently high S/N ratio. Accordingly, highly accurate quantitative analysis can be achieved in comparison with the case of the conventional LC/MS.

Figure 9:
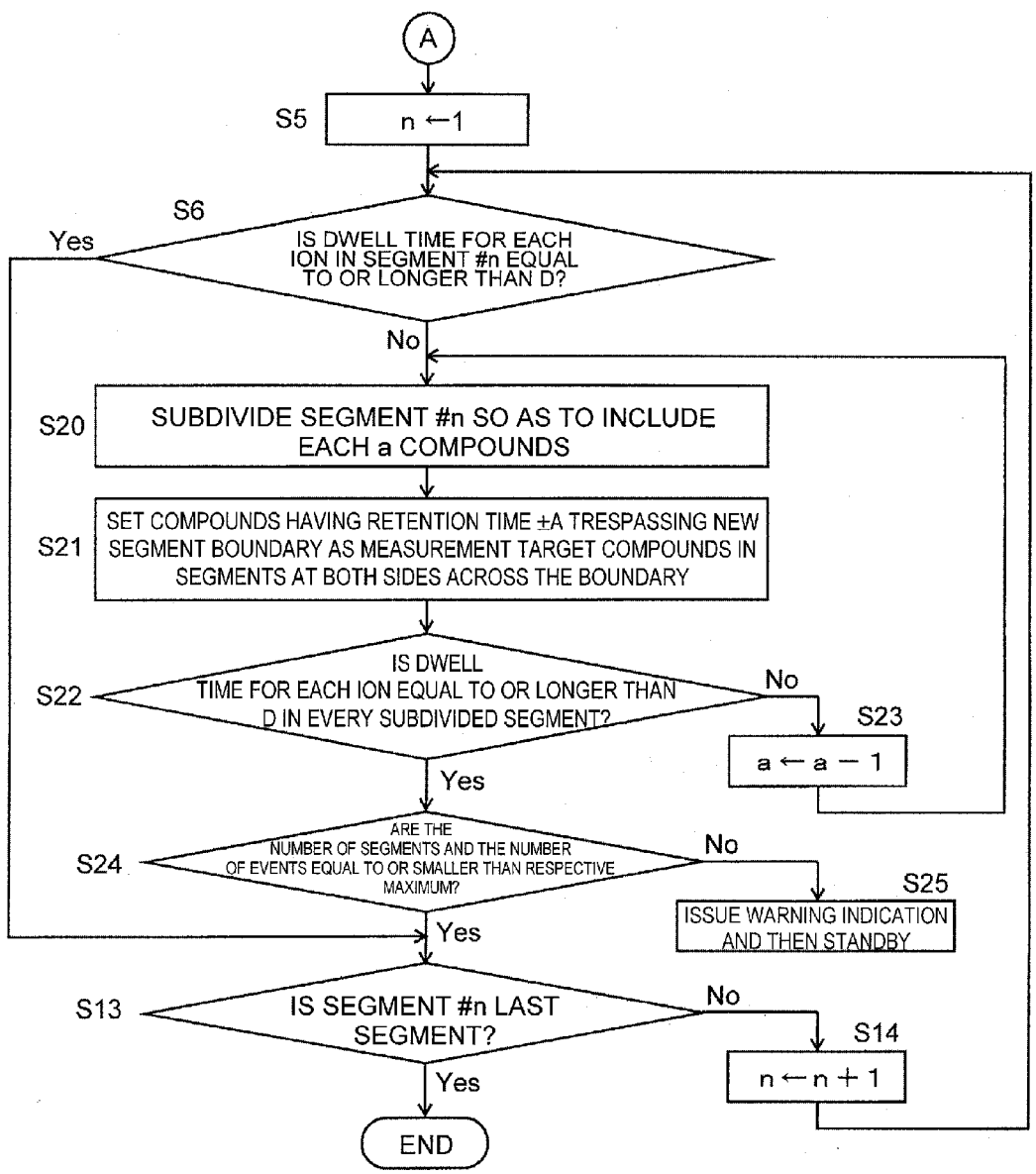
FIG. 9 is a flowchart upon execution of an automatic segment dividing process in an LC/MS of a second embodiment.

Subsequently, an automatic segment dividing process in a second embodiment will be described which is different in the algorithm of the automatic segment dividing process from the case of the first embodiment. FIG. 9 is a flowchart upon the automatic segment dividing process in an LC/MS in the second embodiment, and corresponds to the flowchart of FIG. 4 in the first embodiment. That is to say, the processes of step S1 to S4 are the same as those in the first embodiment. Accordingly, the description of the processes is omitted. Furthermore, the processing details of steps S5 and S6 in FIG. 9 are the same as those of the respective steps in FIG. 4 in the first embodiment.

In the automatic segment dividing algorithm in the first embodiment, the relatively small initial value "c" is set when the segment is subdivided, and the "c" is sequentially increased if the total number of segments and the total number of events exceed the maximum value. This algorithm has advantages of lengthening the dwell time as much as possible within a range where the total number of segments and the total number of events satisfy given conditions by initially subdividing the segments so that the dwell time is the longest, and then gradually shortening the dwell time. As a result, the algorithm is significantly advantageous in accuracy of quantitative analysis.

In contrast, in the automatic segment dividing process in the second embodiment, a relatively large initial value "c" is set for segment subdivision, and the value of "a" is gradually decremented if the dwell time is shorter than the dwell time minimum value (step S23), thereby gradually lengthening the dwell time. That is to say, if it is determined that the dwell time in the segment #n calculated in step S4 is shorter than the dwell time minimum value D (No in step S6), the dwell time in the segment #n does not satisfy the requirement of the dwell time minimum value. Accordingly, subdivision to the relevant segment is attempted in order to lengthening the dwell time. Thus, one segment #n is forcedly subdivided into segments so that "a" number of compounds in an ascending order of the retention time are included in each segment for all compounds assigned to the segment #n. Here, the initial value of "a" is set to, for example, a value which is about ½ of the number of compounds assigned to this segment. In the example in FIG. 5, the number of compounds assigned to the segment #1 is 20. Accordingly, the initial value of "a" is defined as, for example, "11".

Figure 10:
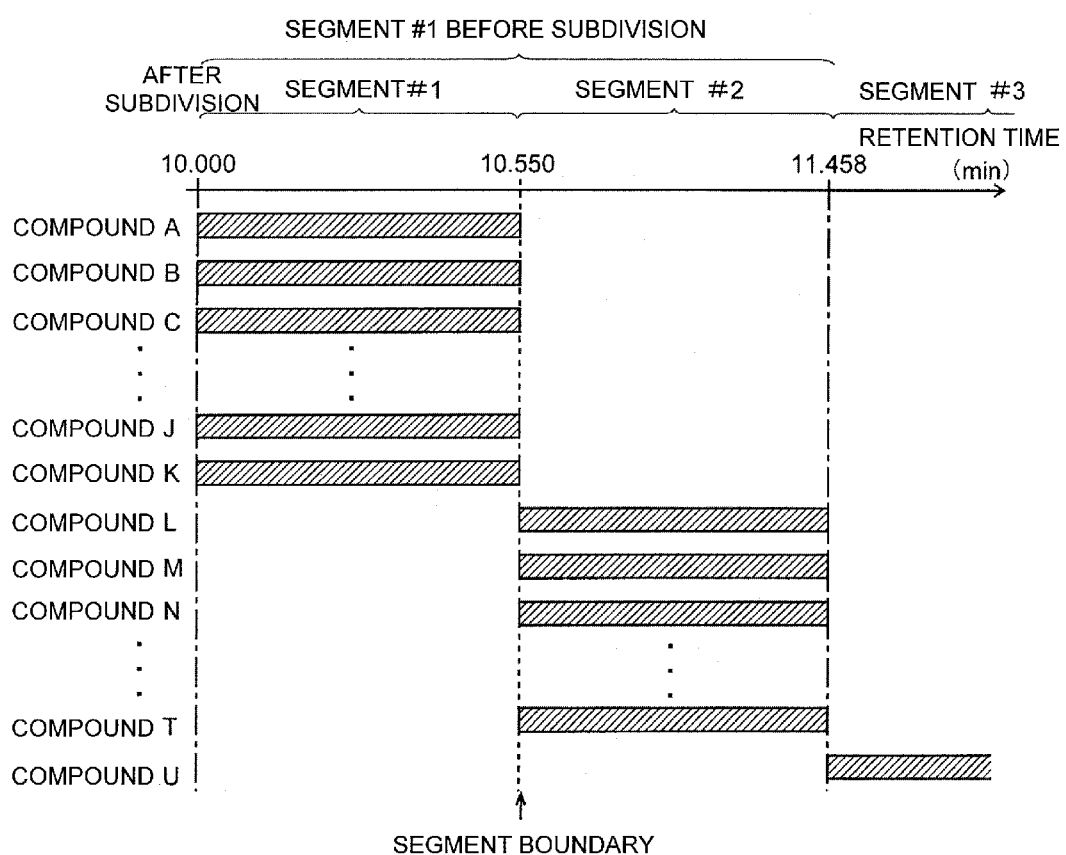
FIG. 10 is a schematic diagram showing an example of a correspondent relationship between segments into which the segment #1 in FIG. 5 is subdivided by an automatic segment dividing process in the LC/MS and compounds in the second embodiment.

That is, in the example in FIG. 5, total 20 compounds A to T are assigned to the segment #1. Accordingly, each 11 compounds is grouped in an ascending order of the retention time to determine a new segment boundary, and the segment #1 is subdivided. As a result, as shown in FIG. 10, one segment #1 before subdivision is subdivided into two. Different 11 compounds (compounds A to K) and 9 compounds (compounds L to T) are assigned to the new segments. The segment boundary may be set at an intermediate time between the retention times of the compounds K and L around the boundary.

Also in this case, the segment boundary is forcedly set. Accordingly, the elution time ranges of some compounds trespass the segment boundaries. Thus, in order to prevent the peak from being lacked even if the position of the peak us deviated, the assignment of the compound which has the elution time range of the retention time±A trespassing the newly set segment boundary is adjusted so that the compound is measured in both segments across the boundary (step S21).

Figure 11:
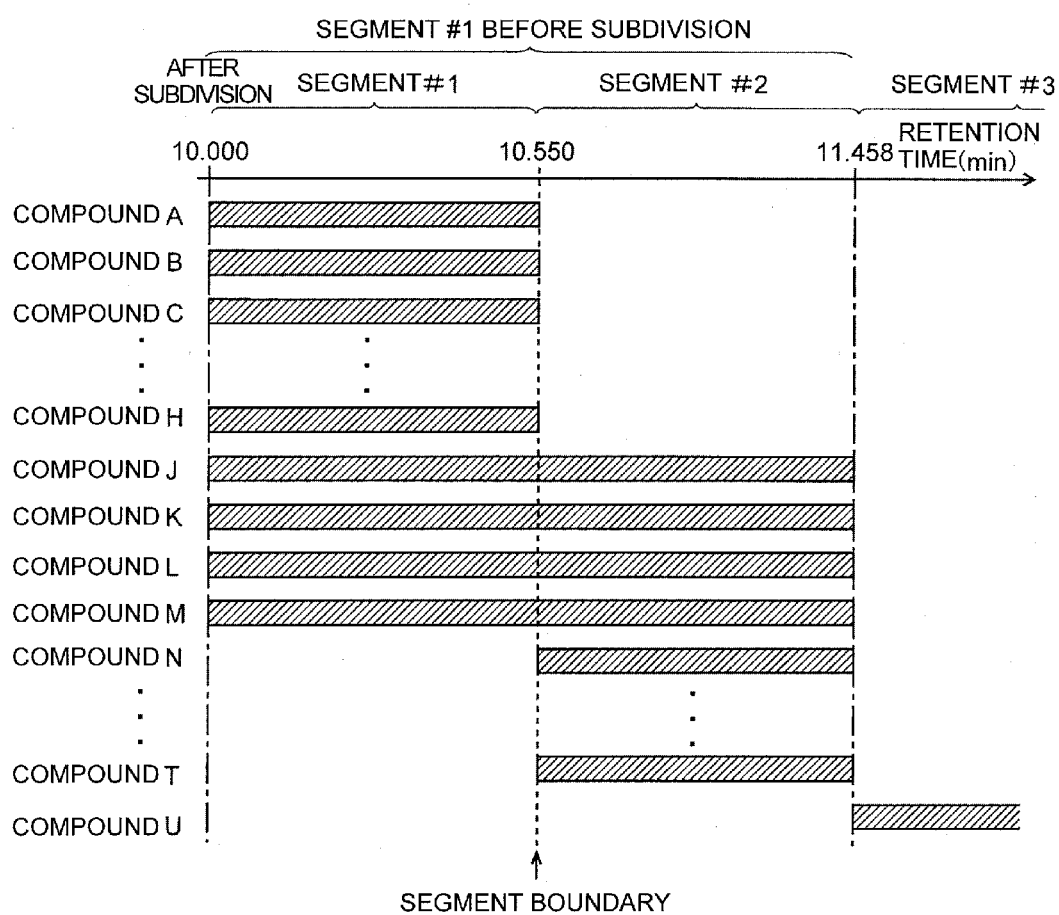
FIG. 11 is a schematic diagram showing an example of the correspondent relationship between segments and compounds after assignment of compounds of which elution time ranges extend over the segment boundary with respect to the segments after reassignment shown in FIG. 10.
Figure 14:
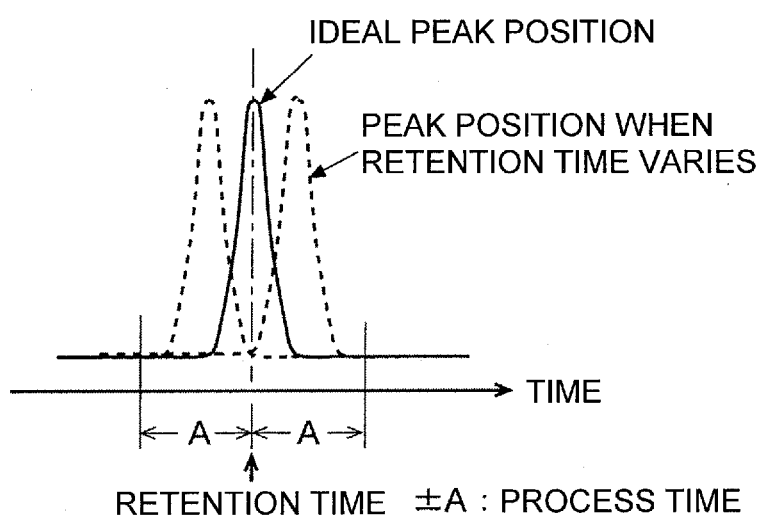
FIG. 14 shows the relationship between the peak of a compound on a chromatogram and retention time and process time.
Figure 15A:
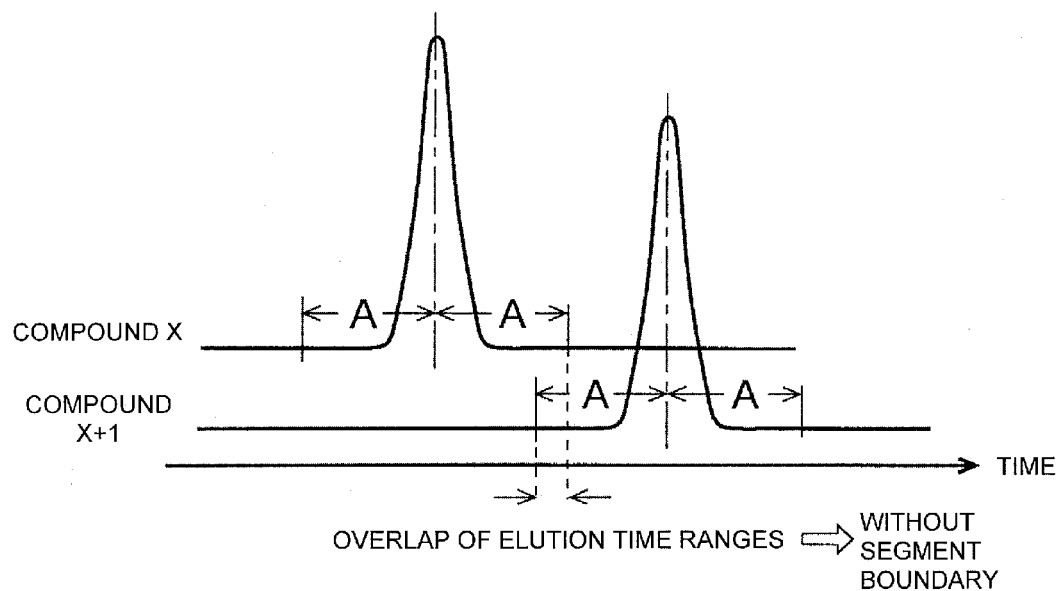
FIG. 15A and FIG. 15B are diagrams showing a chromatogram for illustrating a conventional segment dividing method.
Figure 15B:
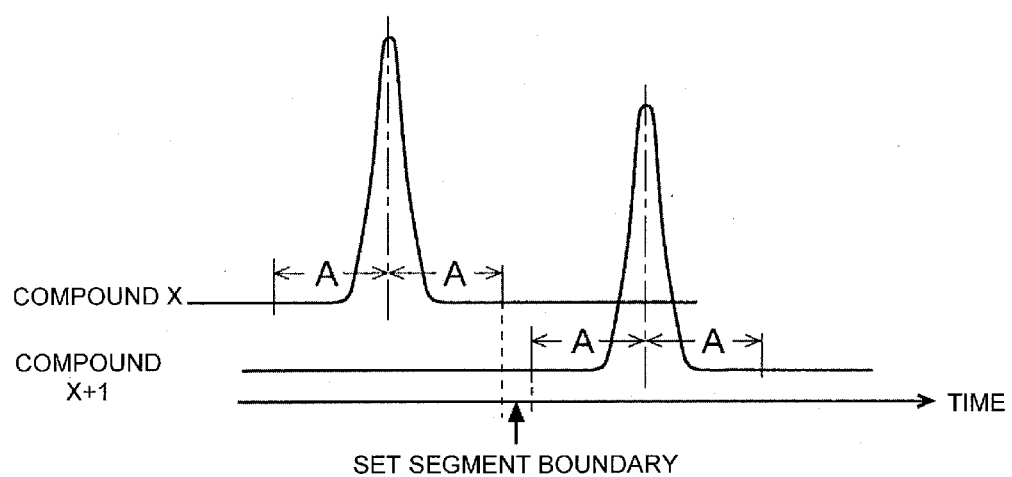

In the example in FIG. 10, the elution time ranges of the compounds J to M trespass the newly created boundaries between the segments #1 and #2. Accordingly, these compounds are assigned not only to the segment #1 but also to the segment #2. For the example in FIG. 10, such compound reassignment is performed for all the compounds included in the segment #1 before subdivision, and the relationship between the segments and compounds as shown in FIG. 11 is acquired.

Next, for each of all the segments newly generated by subdividing the segment #n, it is determined whether the calculated dwell time is equal to or longer than the dwell time minimum value or not (step S22). In the example in FIG. 11, the number of compounds assigned to the segment #1 is 13. Accordingly, the event time is 300 [msec]/13=23 [msec]. The two ions are to be measured for one compound. Accordingly, the dwell time for each ion is (23-2)/2=10.5 [msec]. The number of compounds assigned to the new segment #2 is 11. Accordingly, the event time is 300 [msec]/11=27 [msec] and the dwell time is (27-2)/2=12.5 [msec]. In all the segments newly generated from the segment #1 before subdivision, the dwell time is equal to or longer than the dwell time minimum value. Accordingly, the processing proceeds from step S22 to step S24.

Next, the total number of segments and the total number of events at this time are calculated, and it is determined whether the numbers are equal to or smaller than the maximum value of the number of segments and maximum value of the number of events, respectively, which are previously set in the system (step S24). In the example in FIG. 11, the total number of segments is three and the total number of events is 13+11+1=25. Accordingly, in step S24, it is determined to be Yes, and the processing proceeds to step S13.

If it is determined to be No in step S22, "a" is decremented only by one (step S23), and the processing is returned to step S20. Therefore, repetition of steps S20 to S23 increases the number of segments to be generated through subdivision. This increase, in turn, lengthens the dwell time accordingly, and it is determined to be Yes in step S22. In this case, even if the dwell time is equal to or greater than the dwell time minimum value, the total number of segments and the total number of events exceeding the respective maximum values (No in step S24) causes the warning indication to be output and brings the state into the standby state. Although not shown in FIG. 9, the minimum value of "a" is one. Accordingly, if it is determined to be No in step S22 even with "a" being one, the warning indication is also output.

FIG. 12 shows one example of a parameter table of a measurement method automatically created based on the compound table shown in FIG. 13. In comparison with FIG. 8, the dwell time is generally short. However, the dwell time is maintained at the time equal to or longer 10 [msec] for all the compounds A to U, and the peak area can be calculated based on data having a sufficiently high S/N ratio.

As described above, similarly to the first embodiment, also in LC/MS in the second embodiment, segment subdivision is automatically executed so as to satisfy the dwell time, loop time and process time which are designated by the user, and measurement target compounds are assigned to each segment. SIM measurement according to the thus created measurement method parameter table can acquire an accurate chromatogram peak for every measurement target compound. Accordingly, quantitative analysis can be performed at high accuracy.

It should be noted that the embodiments described above are a mere example of the present invention, and any change, modification or addition appropriately made within the spirit of the present invention will evidently fall within the scope of claims of the present application.

For example, in the embodiments, when the segment having dwell time which does not satisfy the condition is subdivided, a predetermined number ("c" in the first embodiment, and "a" in the second embodiment) of compounds having retention times close to each other are collected to form one segment. Alternatively, instead of the number of compounds, the number of divisions of one segment may be set first, and the segment may be forcedly subdivided. Alternatively, subdivision may be performed according to another algorithm.

For example, in the LC/MS in each of the embodiments, the MS 2 is the single quadrupole mass spectrometer. Also, the present invention is naturally applicable to an LC/MS/MS including an MS unit 2 which is a triple quadrupole mass spectrometer in the case of MRM measurement which requires setting of measurement conditions, such as the elution time range and the mass-to-charge ratio to be measured, for each compound, as with SIM measurement.

Alternatively, it is apparent that the present invention is applicable to a GC/MS and a GC/MS/MS which includes a GC instead of an LC.

REFERENCE SIGNS LIST

1 . . . LC Unit
11 . . . Mobile Phase Container
12 . . . Liquid Transport Pump
13 . . . Injector
14 . . . Column
2 . . . MS Unit
21 . . . Spray Nozzle
22 . . . Heating Capillary
23, 24 . . . Ion Guide
25 . . . Quadrupole Mass Filter
26 . . . Detector
3 . . . Data Processor 4 ... Controller
41 ... Measurement Method Generator
5 ... Storage Device
51 ... Compound Table Storage
52 ... Measurement Method Parameter Table Storage
6 ... Input Unit
7 ... Display Unit
100 ... Input Setting Screen
101 ... Text Input Field
102 ... "Auto-Create" Button

The invention claimed is:

1. A chromatograph mass spectrometer including a combination of a chromatograph for separating compounds in a sample in a temporal direction and a mass spectrometer unit for separating ions originating from the compounds separated by the chromatograph according to mass-to-charge ratios and detecting the ions, the mass spectrometer unit performing selected ion monitoring (SIM) measurement or multiple reaction monitoring (MRM) measurement for one or more specific mass-to-charge ratios at around a chromatogram peak corresponding to a target compound, the chromatograph mass spectrometer comprising:

a) a compound table holding unit which stores a compound table including at least information identifying an estimated retention time or an estimated elution time range and one or more mass-to-charge ratios to be measured, for each of compounds to be measured; and b) a measurement condition information creating unit which creates a measurement condition table including at least information identifying an actual measurement start time, an actual measurement end time and a mass-to-charge ratio to be measured, for each of the compounds to be measured listed in the compound table, based on the information included in the compound table, in order to perform SIM measurement or MRM measurement, wherein the measurement condition information creating unit includes:

b1) a primary segment setting unit which determines a boundary at a time point where the elution time ranges of the compounds included in the compound table do not overlap with each other to set segments each of which is a measurement time unit, and assign one or more compounds to be measured to each segment;

b2) a primary determination unit which, for each of the segments set by the primary segment setting unit, calculates a dwell time, which is data collection time per ion originating from one compound, based on the number of compounds assigned to each segment, loop time which is a previously given measurement point time interval for each ion and the number of ions to be measured for one compound, and determines whether the dwell time is shorter than a previously given dwell time minimum value or not; and b3) a segment dividing process unit which, if the primary determination unit determines that the dwell time calculated for a segment is shorter than the previously given dwell time minimum value, performs segment subdivision and compound reassignment by forcedly dividing one segment into a plurality of segments such that the dwell time is equal to or longer than the minimum value, and arranging a compound having an elution time range trespassing a newly defined segment boundary to be measured in both segments across the segment boundary.

2. The chromatograph mass spectrometer according to claim 1, wherein the measurement condition information creating unit further includes a secondary determination unit which recalculates the dwell time in each segment generated by subdivision for forcefully subdividing one segment into a plurality of segments after the subdivision and compound reassignment, and determines whether the dwell time is shorter than the previously given dwell time minimum value or not, and the segment dividing process unit changes the number of divisions or a division point according to which one segment before subdivision is forcedly subdivided, to newly perform segment subdivision and compound reassignment, if the secondary determination unit determines that the recalculated dwell time is shorter than the dwell time minimum value.

3. The chromatograph mass spectrometer according to claim 2, wherein the segment dividing process unit classifies a plurality of compounds assigned to one segment into groups each including a predetermined number of compounds having retention times close to each other, to determine a new segment boundary.

* * * * *